United States Patent

Rothrum

[11] Patent Number: 5,618,278
[45] Date of Patent: Apr. 8, 1997

[54] SURGICAL FLUID COLLECTION POUCH

[75] Inventor: Robert J. Rothrum, Coon Rapids, Minn.

[73] Assignee: Minnesota Mining and Manufacturing Company, St. Paul, Minn.

[21] Appl. No.: 273,598

[22] Filed: Jul. 11, 1994

[51] Int. Cl.⁶ .............................. A61B 19/00; A61B 19/08
[52] U.S. Cl. .............................. 604/356; 128/853; 128/849
[58] Field of Search ........................ 128/849–856; 604/356, 327; 383/11, 14

[56] References Cited

U.S. PATENT DOCUMENTS

| Re. 24,906 | 12/1960 | Ulrich et al. | 206/59 |
|---|---|---|---|
| 3,133,690 | 6/1962 | Lui | 383/11 |
| 3,452,750 | 7/1969 | Blanford | 128/132 |
| 3,809,077 | 5/1974 | Hansen | 128/132 D |
| 3,865,770 | 2/1975 | Blake | 260/27 R |
| 4,169,472 | 10/1979 | Morris | 128/132 D |
| 4,323,062 | 4/1982 | Canty | 128/132 D |
| 4,413,080 | 11/1983 | Blake | 524/187 |
| 4,559,937 | 12/1985 | Vinson | 128/132 D |
| 4,569,960 | 2/1986 | Blake | 524/145 |
| 4,570,628 | 2/1986 | Neal | 128/132 D |
| 4,598,458 | 7/1986 | McAllester | 128/132 D |
| 4,869,271 | 9/1989 | Idris | 128/853 |
| 4,890,628 | 1/1990 | Jackson | 128/849 |
| 4,974,604 | 12/1990 | Morris | 128/853 |
| 4,976,274 | 12/1990 | Hanssen | 128/849 |
| 5,019,071 | 5/1991 | Bany et al. | 604/389 |
| 5,038,798 | 8/1991 | Dowdy et al. | 128/853 |
| 5,042,507 | 8/1991 | Dowdy | 128/849 |
| 5,074,316 | 12/1991 | Dowdy | 128/849 |
| 5,125,995 | 6/1992 | D'Haese et al. | 156/155 |
| 5,158,557 | 10/1992 | Noreen et al. | 604/389 |
| 5,270,111 | 12/1993 | D'Haese et al. | 428/356 |

FOREIGN PATENT DOCUMENTS

| 2018597 | 10/1979 | United Kingdom . | |
| 2148125 | 5/1985 | United Kingdom | 128/846 |
| WO93/07914 | 10/1992 | WIPO | A61L 31/00 |

*Primary Examiner*—David Isabella
*Assistant Examiner*—Dennis Ruhl
*Attorney, Agent, or Firm*—Gary L. Griswold; Walter N. Kirn; F. Andrew Ubel

[57] ABSTRACT

The present invention provides a fluid collection pouch which may be easily attached to a surgical drape or directly to a patient's skin. The fluid collection pouch comprises a front panel and a rear panel joined along common side edges (thus defining a fluid receiving chamber). The pouch has an open top end to which is adhesively attached a portion of a tape attachment strip. A second portion of the tape attachment strip overhangs the open top end of the pouch and is covered with a liner. In use, the liner is removed (thus exposing an additional portion of the adhesive surface of the tape attachment strip) and the exposed adhesive is placed against the surface to which the pouch is being attached. This design provides a leak free seal between the surface and the pouch, and fluid is able easily to flow over the sealed region into the pouch without being inhibited or directed away. The present invention also provides a fenestrated surgical drape having a pre-attached fluid collection pouch and methods of making such fluid collection pouches and drapes.

20 Claims, 7 Drawing Sheets

SURGICAL FLUID COLLECTION POUCH

RELATED APPLICATIONS

Of related interest is U.S. patent application "Novel Surgical Drapes Having Tape Attachment Strips", Attorney Docket No. 50597USA1A, Ser. No. 08/273,500, now allowed, Express Mail Certificate No. RB710214494, filed on even date herewith by the assignee of this invention, which is herein incorporated by reference.

FIELD OF THE INVENTION

This invention relates to surgical fluid collection pouches and to tapes used to secure fluid collection pouches to a surgical drape or to a patient. This invention also relates to surgical drapes having such pouches attached thereto.

BACKGROUND OF THE INVENTION

Many surgical procedures result in the production of rather large quantities of fluids (e.g., blood and irrigation liquids) which need to be removed from the operating site. Removal of the fluids can be accomplished in a number of ways. One of the oldest methods of controlling fluids is to use absorptive devices such as towels, sponges and pads which have been sterilized to lessen the risk of infection. Alternatively, suction devices may be used to remove fluids from the operatory site.

As part of good sterile technique, it is a common goal to keep the patient, the operating personnel and the room as clean, dry and bacteria free as possible. This is especially crucial in the control of infectious disease containing fluids such as blood. In certain surgical techniques, large amounts of fluid are released or used. In such cases, absorptive devices and/or suction devices are oftentimes insufficient or impractical for removal of fluids from the operation site. As a result, there is a recognized need for a surgical drape which permits the effective collection of fluids created and/or released during a surgical procedure. Modifications have been made to the surgical drape itself to help direct and/or collect the fluids. Such modifications have been accomplished by creating folds and tucks in the drapes to form pockets for collecting fluids or by attaching separate pieces of material to the exterior surface of the drape to form pockets for trapping or collecting fluids.

An alternate solution has been to attach pouches to the drape to collect the fluids resulting from the operation. Unfortunately, previous methods used to attach fluid collection pouches to surgical drapes have been either expensive or offer poor performance. For example, one method of attaching a pouch to a drape involves the use of an adhesive strip or a double-sided adhesive tape. Unfortunately, it is difficult to place precisely the adhesive strip or tape at the leading edge of the pouch (i.e., at the edge of the pouch closest to the surgical site). As a result a tab of non-adhered pouch material is often left at the leading edge of the pouch and fluid is inhibited from running directly into the pouch. Another method of attaching fluid collection pouches to drapes involves sonically bonding or heat bonding the pouch to the drape. Unfortunately, this technique does not allow the user to secure the pouch at the time of use (e.g., in a custom position).

What is needed is a pouch which can be easily attached to a drape (e.g., at the point of use), which provides a leak-free seal to the drape, and which allows fluid to flow directly into the pouch without being inhibited or directed away.

SUMMARY OF THE INVENTION

The present invention provides a fluid collection pouch which may be easily attached to a surgical drape or directly to a patient's skin. The fluid collection pouch comprises a front panel and a rear panel joined along common side edges (thus defining a fluid receiving chamber). The pouch has an open top end to which is adhesively attached a portion of a tape attachment strip. A second portion of the tape attachment strip overhangs the open top end of the pouch and is covered with a liner. In use, the liner is removed (thus exposing an additional portion of the adhesive surface of the tape attachment strip) and the exposed adhesive is placed against the surface to which the pouch is being attached. This design provides a leak free seal between the surface and the pouch, and fluid is able easily to flow over the sealed region into the pouch without being inhibited or directed away.

The present invention also provides a surgical drape having a pre-attached fluid collection pouch. The surgical drape includes a main sheet with a fenestration to allow access to the surgical site. Attached to the main sheet is a fluid collection pouch made from a fluid impervious material such as plastic film. The fluid collection pouch comprises a front panel and a rear panel joined along common side edges (thus defining a fluid receiving chamber). The pouch has an open top end positioned adjacent the fenestration in the main sheet. The fluid collection pouch is attached to the drape using a tape attachment strip comprising a backing and a layer of adhesive on one side of said backing. The tape attachment strip provides a "ramp" over which fluids easily may flow.

Optionally formed from the front and rear panels of the pouch are a pair of troughs which extend upwardly from the open top end of the fluid collection pouch along the common side edges such that the troughs and the open top end of the pouch surround at least a portion of the surgical site. The troughs are designed to open inwardly toward the surgical site so as to contain and channel fluids into the open top end of the fluid collection pouch. Each of the fluid troughs has an upper flap formed from the front panel of the fluid collection pouch and a lower flap formed from the rear panel of the pouch. The lower flaps of the troughs are adhesively attached to the surface (e.g., a surgical drape with a fenestration) using two additional tape attachment strips as previously described.

The fluid collection pouch may be fitted with a sieve adjacent the opening to trap and collect objects such as instruments and sponges which may fall into the pouch during a surgical procedure. A drainage opening also may be placed in the pouch to allow removal of fluids from the pouch.

To keep the troughs and the fluid collection pouch open during use, malleable opening strips may be attached to the inside or outside of the troughs and pouch opening. Once the pouch is in place, the malleable strips may be bent and shaped to maintain the troughs and the pouch opening in an open position.

BRIEF DESCRIPTION OF THE DRAWINGS

FIGS. 2a–2c are alternative cross-sectional views of the fluid collection pouch of the present invention taken along line 2—2 of FIG. 1a;

FIG. 4 is a cross-sectional view of the surgical drape and fluid collection system of FIG. 3a taken along line 4—4 of FIG. 3a;

FIG. 7 is a cross-sectional view of the fluid collection pouch of the present invention taken along line 7—7 of FIG. 1a.

DETAILED DESCRIPTION OF THE INVENTION

The present invention provides a fluid collection pouch comprising: a front panel and a rear panel joined along common side edges and defining a fluid impervious receiving chamber therein and with an open top end; and a tape attachment strip having a backing, an adhesive layer covering one side of said backing, and a liner, wherein a portion of the tape attachment strip is adhesively attached to the rear panel along the open top end and wherein the liner covers that portion of the adhesive layer which is not attached to the rear panel.

The fluid collection pouch is constructed from a fluid impervious material. Examples of suitable fluid impervious materials include plastic sheet materials of polymers such as acetate, ethylene vinylacetate (EVA), rayon, triacetate, acrylic, aramid, nylon, olefin {e.g., poly(1-butene), polycarbonate, polyethylene, polyester, poly(3-methyl-1-butene), poly(1-pentene), polypropylene, and polystyrene}, polysulfone, polytetrafluoroethylene, poly(vinyl alcohol), poly(vinyl chloride), poly(vinylidene chloride), poly(vinylidene fluoride), natural rubber, polyisoprene, polybutadiene, diene styrene copolymers, ethylene propylene copolymers, ethylene propylene diene terpolymers, styrene butadiene block copolymers, styrene isoprene block copolymers, and polyurethane.

Preferred fluid impervious materials are heat bondable (e.g., so as to allow two sheets to be later sonically joined to provide a fluid impervious joint) and sterilizable (e.g., able to withstand the temperatures, radiation and gases used during the sterilization process which includes temperatures in excess of 60° C. for ethylene oxide sterilization, and temperatures in the range of from 120° to 135° C. for steam sterilization).

Preferred plastic sheet materials include acetate, ethylene vinyl acetate, acrylic, nylon, polypropylene, polyethylene, and polyester. Most preferred plastic sheet materials include polyethylene films. Preferred plastic sheet materials are nontoxic, more preferably hypoallergenic, and are most preferably also environmentally safe (e.g., may be recycled or disposed of in a manner which does not harm the ecosystem). A particularly well suited film material for ethylene oxide sterilization is polyethylene.

A tape attachment strip (comprising a backing, an adhesive layer, and a liner) is used to attach the fluid collection pouch to a surface (e.g., a surgical drape or a patient's skin). The tape attachment strip provides a "ramped" transition between the surface and the pouch. As a result, fluids are able to flow readily over the ramp and into the pouch.

The tape attachment strip allows for great flexibility and economy for the user. Pouches which comprise the tape attachment strip may be positioned easily and attached to a variety of standard surgical drapes. This allows the user to "customize" a standard type of drape in instances where fluid collection is desired. As a result, fewer styles of specialized drapes (e.g., drapes which incorporate pouches) must be inventoried by the hospital.

In addition, the tape attachment strip described herein provides a cost effective method whereby a drape manufacturer can assemble specialized drapes (e.g., from their standard drapes). The tape attachment strip of the present invention is compatible with most drape and pouch materials and can easily be cut to size and assembled into the finished specialized drape. In contrast, some drape and pouch materials can not be sonically or heat bonded together.

In a preferred embodiment, the tape attachment strip comprises a "single-sided" pressure sensitive adhesive tape (i.e., a tape comprising a backing and a pressure sensitive adhesive, "PSA", coated on one side of said backing) which is partially affixed to the edge of the rear panel (i.e., to the edge or edges which are adjacent to or surround the surgical site) of the pouch. This leaves a portion of the single-sided adhesive tape free for attachment to the surface. The free portion of adhesive tape is preferably protected, prior to use, with a liner. The liner may be easily peeled away from the tape to expose the adhesive. The tape attachment strip preferably comprises a slit liner, thus facilitating easy attachment of the tape to the pouch. In use, a first portion of the liner is removed (thus exposing a strip of adhesive along the length of the tape) and the exposed portion of adhesive is placed against the pouch to which the tape attachment strip is being attached. This technique avoids the necessity of maintaining precise alignment of the tape to the edge of the pouch.

Suitable single-sided adhesive tapes for use in the present invention include commercially available single-sided medical tapes. For example, No. 1523 tan 0.13 mm polyethylene medical tape; No. 1526 transparent 0.13 mm polyethylene medical tape; No. 9830 transparent 0.07 mm polyethylene medical tape; No. 9833 white 0.14 mm polyethylene medical tape; and No. 9838 white medical tape having a paper backing and a water-dispersible adhesive are suitable for use in the present invention with disposable drapes. No. 9838 white medical tape is suitable for use in the present invention with reusable drapes. Nos. 1523, 1526, and 9830 medical tapes have matte finishes on the non-adhesive surface. All of the tapes are coated on one surface with a hypoallergenic, pressure sensitive acrylate adhesive and are wound with a bleached Kraft paper liner (optionally slit lengthwise) having a silicone-treated, polyethylene coated surface. The liner (or a portion of the liner) may be separated from the tape during application of the tape to the pouch. All of the above-identified commercially available tapes are available from Minnesota Mining and Manufacturing Company of St. Paul, Minn., U.S.A. Most of these medical tapes are identified in 3M *Medical Specialties Product Reference Guide* published by 3M Health Care in 1991 and available from 3M Medical Specialties Department, the disclosure of which is incorporated by reference herein. The remainder of these medical tapes are also available in publications from 3M Medical Specialties Department.

Suitable adhesives for use in the present invention include those pressure sensitive adhesives which are capable of providing the necessary amount of peel strength and/or shear strength to function in the manner required (e.g., sufficient strength to attach securely the pouch to the surface without unintended detachment). Preferred adhesives for use in the medical field should be non-toxic, more preferably hypoallergenic, and are most preferably also environmentally safe.

Suitable pressure sensitive acrylate adhesives for use in the present invention include, for example, copolymers which are reaction products of the polymerization of at least one "A" monomer and at least one "B" monomer to yield a copolymer having an inherent viscosity of about 1.0 dl/g to about 2.0 dl/g. The A monomer is a polymerizable monomer comprising an acrylate or methacrylate ester of a non-tertiary alcohol or a mixture of non-tertiary alcohols with the alcohols having from 1 to 14 carbon atoms and desirably averaging about 4 to 12 carbon atoms. The B monomer is an ethylenically unsaturated compound and desirably may be acrylic acid, methacrylic acid, itaconic acid, acrylamide, methacrylamide, acrylonitrile, methacrylonitrile, vinyl acetate, N-vinyl pyrrolidone, or combinations thereof. The A monomer is polymerizable and contributes the viscoelastic properties of the pressure sensitive adhesive copolymer. Non-limiting examples of such A monomers include the esters of acrylic acid or methacrylic acid with non-tertiary alkyl alcohol such as 1-butanol, 1-pentanol, 2-pentanol, 3-pentanol, 2-methyl-1-butanol, 1-methyl-1-butanol, 1-methyl-1-pentanol, 2-methyl-1-pentanol, 3-methyl-1-pentanol, 2-ethyl-1-butanol, 2-ethyl-1-hexanol, 3,5,5-trimethyl-1-hexanol, 3-heptanol, 2-octanol, 1-decanol, 1-dodecanol, and the like. Such monomeric acrylic or methacrylic esters are known in the art, and many are commercially available. The B monomer is an ethylenically unsaturated compound copolymerized with the A monomer to affect the physical properties of the resulting pressure sensitive adhesive copolymer. In general, the presence of the B monomer will reduce the flexibility of the resulting pressure sensitive adhesive copolymer. Thus, the weight percentages of the A monomer and the B monomer should be balanced in order to provide a pressure sensitive adhesive copolymer having an inherent viscosity of from about 1.0 dl/g to about 2.0 dl/g. The weight percentage ratio of A monomer: B monomer ranges from about 85:15 to about 98:2 and desirably from about 90:10 to 97:3.

The pressure sensitive adhesive copolymer should be tacky at room temperature as well as at skin temperature of mammals. Also, the adhesive should be hypoallergenic, i.e., after continuous contact with skin, there is no significant skin sensitization or irritation during adhesion. Often, to determine if an adhesive is hypoallergenic, the following evaluations are conducted: cell cytotoxicity, skin irritation, and sensitization potential. The United States Food and Drug Administration recommends such evaluations in a Tripartite Biocompatibility Draft Guidance for Medical Devices. The commercially available medical tapes described herein using acrylate pressure sensitive adhesives of the type described herein are generally considered hypoallergenic. Presently preferred as an acrylate pressure sensitive adhesive for tapes used in the present invention is an isooctyl acrylate/acrylic acid copolymer in a weight ratio of about 94:6. The inherent viscosity of the copolymer is about 1.4–1.6 dl/g. Preferably, acrylate pressure sensitive adhesives have a tackifier added to the formulation to improve tack. Commercially available tackifiers include, for example, "FORAL" branded colophony acid rosins, such as "Foral AX" and "Foral 85" rosins, commercially available from Hercules Corporation, and partially hydrogenated methylstyrene hydrocarbon resins, such as "Piccolastic A25" resin, also commercially available from Hercules Corporation. Such tackifiers can be added during preparation of the acrylate pressure sensitive adhesive in an amount of about 35–40 weight percent of the copolymer solids.

Alternate pressure sensitive adhesives useful in the present invention include, for example, hypoallergenic Kraton rubber-based pressure sensitive adhesives produced using styrene-butadiene or styrene-isoprene copolymers commercially available as KRATON branded copolymers from Shell Oil Company of Houston, Tex. A variety of Kraton based pressure sensitive adhesives are disclosed in U.S. Pat. Nos. 5,019,071 (Bany et al.) and 5,158,557 (Noreen et al.), the disclosures of which are incorporated by reference herein. Preferred as Kraton rubber-based pressure sensitive adhesives are Kraton 1107, Kraton 1111, Kraton 1101, and Kraton D branded copolymers, tackified with compatible tackifiers such as ESCOREZ™ 1310LC branded tackifier commercially available from Exxon Chemicals, a solid $C_5$ tackifying resin commercially available as WINGTACK™ Plus brand tackifier from Goodyear Tire and Rubber Company, Akron, Ohio and naphthenic oils having 10% aromatics commercially available as SHELLFLEX™ 371 from Shell Oil Company. Such tackifiers can comprise about 45 to about 70 weight percent of the pressure sensitive adhesive, while the Kraton copolymer can comprise about 30 to 55 weight percent. Presently preferred is a Kraton based pressure sensitive adhesive comprising about 35 weight percent Kraton 1111, about 53 weight percent Wingtack Plus, about 11 weight percent Shell flex 371, and about 2 weight percent Irganox 1010 and 1076 branded antioxidants, in a similar formulation to that disclosed in Examples 1–13 of U.S. Pat. No. 5,019,071.

Additional alternate and presently preferred pressure sensitive adhesives useful in the present invention include, for example, the water-dispersible pressure sensitive adhesives disclosed in U.S. Pat. Nos. 3,865,770; 4,413,080; 4,569,960; 5,125,995; and 5,270,111 and in U.S. patent application Ser. Nos. 07/763,823; 07/889,647; and 08/093,080 the disclosures of which are herein incorporated by reference.

Pressure sensitive adhesive copolymers can be copolymerized using known polymerization techniques such as emulsion polymerization and solution polymerization. Sources of polymerization preparation and techniques include *Organic Polymer Chemistry,* Saunders et al. (Halsted Publishing Company, New York 1973); *Applied Polymer Science,* Tess et al. (American Chemical Society, Washington, D.C. , 1981); *Principles of Polymerization,* Odien (John Wiley and Sons, New York, 1981); and the *Handbook of Pressure-Sensitive Adhesive Technology, Second Edition,* Satas, Ed., (Van Nostrand Reinhold Company, New York, 1989), the disclosures of which are incorporated by reference. Specifically, acrylate pressure sensitive adhesive copolymers can be prepared according to U.S. Pat. No. 2,884,126/RE 24,906 (Ulrich), the disclosure of which is incorporated by reference herein. The presently preferred acrylate copolymer pressure sensitive adhesive can be prepared by emulsion polymerization according to Example 5 of U.S. Pat. No. 2,884,126/RE 24,906, except that tackifier is added to the emulsion in an amount of about 35–40% weight percent of copolymer solids, and that tackified copolymer is dissolved in a heptane-isopropanol (70:30) solution. The presently preferred Kraton copolymer pressure sensitive adhesive can be prepared in the manner as disclosed in Examples 1–13 of U.S. Pat. No. 5,019,071, the disclosure of which is incorporated by reference above.

The adhesive surface of the tape attachment strip is preferably covered prior to use with a suitable liner. Suitable liners comprise any materials which adequately cover the adhesive (thus preventing contamination of the adhesive tack) and which can be easily peeled apart from the adhesive. Preferred liners have a low adhesion coating (such as a silicone treated polyethylene coating) which facilitates the easy peeling apart of the liner.

More preferably, the adhesive tape is initially provided with a liner that has been slit lengthwise into at least two narrower pieces (or "strips"). A first lengthwise piece of liner is removed by the manufacturer or end user to expose a first portion of the adhesive surface. This first portion of adhesive surface is then contacted with the inside surface of the rear panel of the pouch. The second liner portion is temporarily left in place and is removed when the pouch is to be attached to the surface. When it is desired to attach the pouch to a surface, the user or manufacturer peels off the remaining portion of the liner and attaches the exposed adhesive to the surface.

Figure 9A:
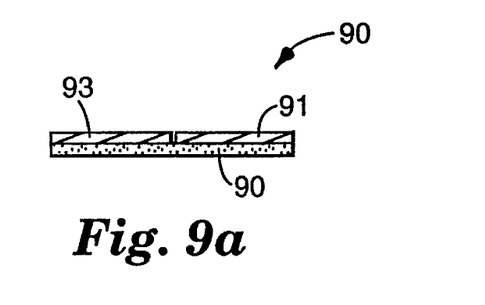
FIGS. 9a, 9b, and 9c are side views of the tape attachment strip of FIG. 8 taken along lines 9a—9a, 9b—9b, and 9c—9c, respectively.
Figure 9B:
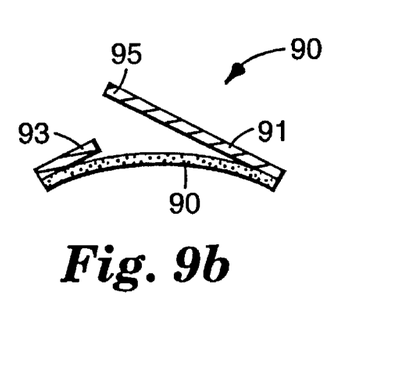
Figure 9C:
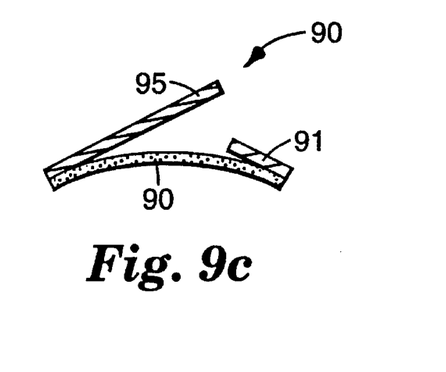
Figure 10A:
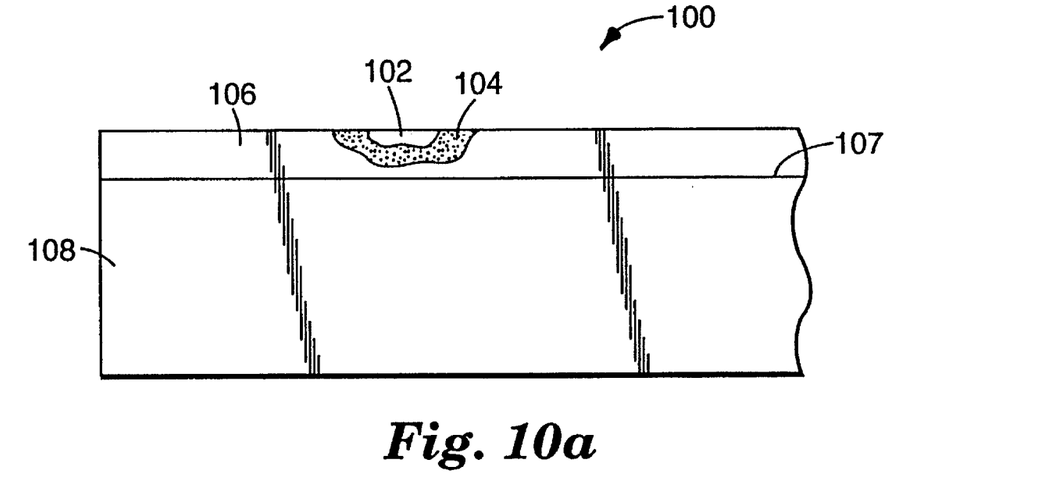
FIGS. 10a and 10b are plan views of the liner side of a presently preferred tape attachment strip of the present invention, wherein the liner has been slit lengthwise and a portion of the tape and liner have been folded to facilitate removal of the liner from the tape during use.
Figure 10B:
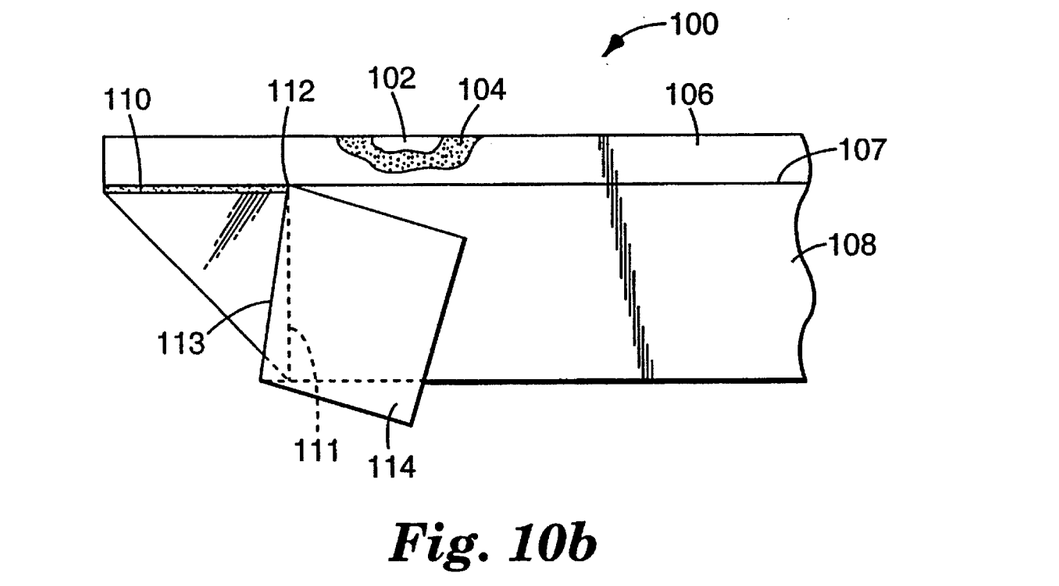

The slit which separates the liner strips may be either a straight line or a curved line (e.g., a sinusoidal line) running the length of the tape. In addition, the liner may be slit into two or more equal width strips of liner or into two or more different width strips of liner. In general, a straight line slit has the advantage of being simple to produce. Alternatively, a curved line slit such as a "sinusoidal" slit has the advantage of providing integral "tabs" of liner when the tape backing is flexed along the slit line. In use, when a tape having a sinusoidally slit liner is flexed along the slit (as shown in FIGS. 9 and 10), a portion of the liner lifts away from the underlying tape. This lifted portion can then be easily grasped and the liner peeled apart from the tape.

The single-sided adhesive tape attachment strip has several advantages over double-sided adhesive tapes. Notably, single-sided adhesive tapes are generally less expensive to produce than double-sided adhesive tapes. In addition, the single-sided adhesive tape attachment strip is easy to attach at the edge of a pouch (i.e., without the need for precise alignment) and provides a ramp over which fluids may easily flow. In contrast, double-sided adhesive tapes are difficult to align and attach precisely at the edge of a pouch. Thus, a non-adhered portion of the pouch edge is often left exposed. This non-adhered portion can inhibit fluid flow into the pouch.

The drape itself may be made from any number of materials (e.g., disposable or reusable materials) and combinations thereof. Breathable materials such as woven and nonwoven materials may be used in the construction of the drape. Such materials are desirable in that they are breathable and therefore allow air circulation and provide an added degree of comfort to the patient. Alternatively, a fluid impervious material such as plastic film may be used as the sheet material or a combination of nonwoven and film materials may also be used. For example, the drape, as a whole, may be made from a breathable nonwoven material and the area surrounding the fenestration may be made fluid impervious (e.g., by adding a layer of plastic film or by treating the nonwoven material with a coating of fluid impervious material) and/or fluid absorbent material (e.g., by adding a layer of absorbent material such as DRYSITE™ available from Johnson and Johnson Medical Inc.).

Preferred drape fabrics for use in the present invention include those fabrics described in U.S. Pat. No. 3,809,077 (Hansen); U.S. patent application No. 08/105,430; and PCT Patent Application WO 93/07914 (Weimer et al.), which are herein incorporated by reference. Suitable drape fabrics for use in the present invention also include commercially available drape fabrics such as SONTARA™ (e.g., #8018) nonwoven polyester fabrics (available from E. I. DuPont DeNemours Company and presently believed to be used in drapes made by Johnson and Johnson Medical Inc. and Baxter Healthcare Corp.) and spunbond/meltblown/spunbond laminate materials (available from Kimberly-Clark Corp. and sold under the trademark EVOLUTION™ Fabric System). The pouch system of the present invention may be easily attached by the user (e.g., surgeon or nurse) to either a disposable or reusable drape or may be attached by a manufacturer (e.g., to create a specialized drape).

The collection pouches shown in the figures are generally triangular in shape and have drainage openings fitted with a drain nozzle located in the bottom-most portion of the pouch. This triangular design is the most advantageous since it directs the fluids collected within the pouch to a point adjacent the drain opening thereby allowing the majority of the fluid to be drained from the pouch if so desired. Note, however, that other shapes and sizes of pouches (e.g., rectangular or circular pouches) also may be used in conjunction with the present invention. The actual size and shape of the pouch will be governed primarily by the end use of the drape. In operations which generate large amounts of fluids, larger pouches may be desirable. However, it should be understood that as the fluid level in the pouch increases, so does the weight. Thus, in such cases it may be desirable to either periodically or continuously drain the fluids from the pouch.

The advantages of the present invention stem from the unique flow transition from the surface to the fluid collection system as a result of the unique tape attachment strips which attach the system to a drape or to a patient's skin. The optional integral troughing and collection system provides effective lateral barriers to fluid run-off and also provides an efficient means for channeling fluids into the fluid collection pouch. In addition, the present invention also provides advantages related to ease of manufacture and has a lower cost.

As described in the preceding portions of the application, the fluid collection system has a front panel and a rear panel. These panels may be separate pieces which are joined (e.g., sonically bonded or adhesively joined) at their edges. Alternatively, the fluid collection system may be formed from a single piece of material which is folded over and then joined, thereby reducing the number of seams which must be closed in order to form a fluid-tight construction.

Preferably, the entire drape and pouch system (including the tape attachment strip) should be capable of being sterilized. Several different sterilization processes are used in the medical field. For example, steam autoclave, gamma radiation, and ethylene oxide may be employed. Preferred drape and pouch systems should withstand at least one cycle through the desired sterilization process. For example, preferably the drape and pouch system should remain functional after irradiation with up to at least 25 kGys gamma cobalt-60 radiation, a dosage often used for sterilization of medical devices.

DETAILED DESCRIPTION OF THE DRAWINGS

Reference is made to FIGS. 1–10 wherein like parts have been given like index numbers. Throughout the drawings the various layers of tape, adhesive, or liner have been exaggerated in thickness for purposes of illustration and clarity. In particular, the adhesive layer is shown in exaggerated thickness. In addition, the size of the various components may be modified, if desired, to accommodate the particular needs of the drape or pouch.

Figure 1A:
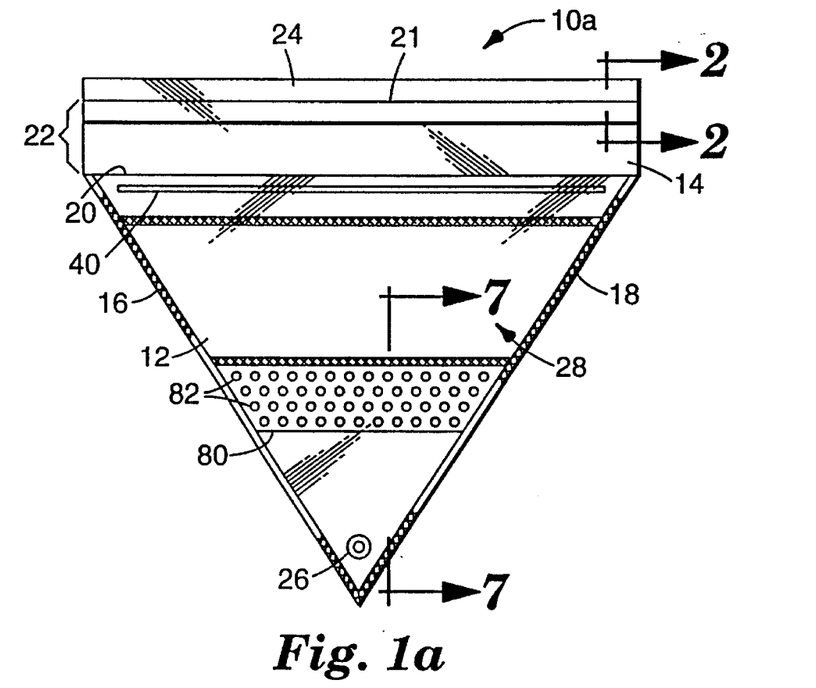
FIG. 1a is a top plan view of a fluid collection pouch of the present invention.
Figure 1B:
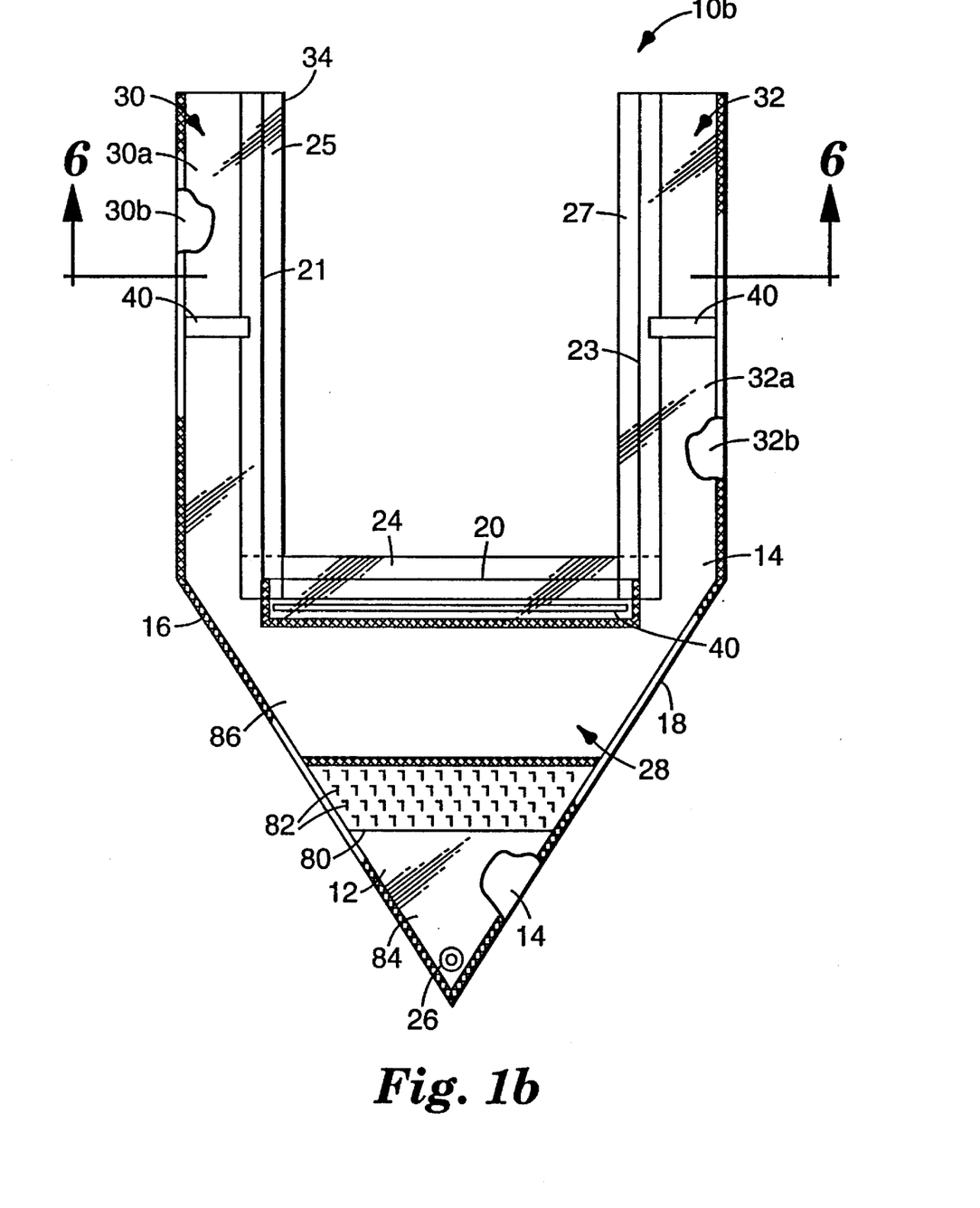
FIG. 1b is a top plan view of a fluid collection pouch of the present invention.

Referring to FIGS. 1a and 1b, there is shown a fluid collection pouch system (10a and 10b) for attachment to a surgical drape or to a patient's skin. As shown in FIG. 1a, the pouch system 10a has a triangular pouch 28 comprising a front panel 12 and rear panel 14 joined along common side edges (left 16, right 18) to define a fluid receiving chamber with an open top end 20. As shown in FIG. 1b, the fluid collection pouch system 10b has a triangular pouch 28 comprising a front panel 12 and rear panel 14 joined along common side edges (left 16, right 18) to define a fluid receiving chamber with an open top end 20 and two troughs (left 30, right 32). The front panel 12 of the fluid collection pouch system 10b is a one piece construction wherein the front of the collection pouch and the left and right troughs are integrally formed from the same piece of material. To form the troughs 30 and 32 and to allow access to a surgical site, the front panel 12 and rear panel 14 have a rectangular or "U" shaped cut-out portion 34, thereby defining the left trough 30 and the right trough 32.

Figure 6:
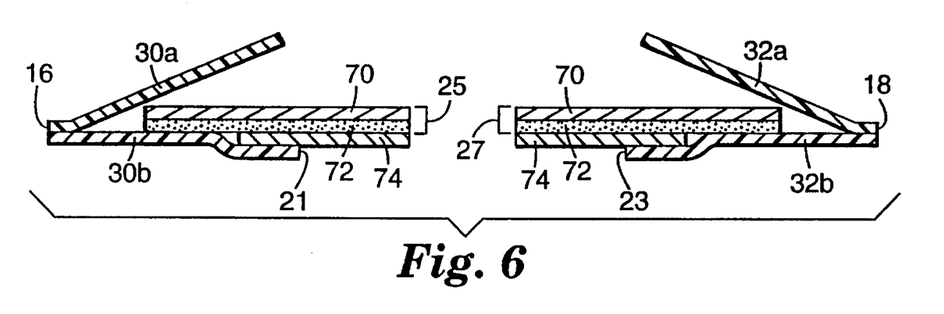
FIG. 6 is a cross-sectional view of the fluid collection pouch of the present invention taken along line 6—6 of FIG. 1b.

Turning to both FIG. 1b and FIG. 6, the left and right troughs (30 and 32) each have an upper flap (30a and 32a) which are part of from panel 12 and a lower flap (30b and 32b) which are part of the rear panel 14. Upper and lower flaps 30a and 30b are joined along common edge 16 while upper and lower flaps 32a and 32b are joined along common edge 18.

To keep the pouch 28 and the troughs 30 and 32 open during use, malleable opening means or strips 40 may be attached to the troughs 30 and 32 and the open top end 20 of pouch 28. The malleable strips 40 may be made from any number of materials such as plastic, metal or plastic coated metal. The primary attributes of the material are that it is moldable, noncorrosive, sterilizable and readily attachable to the material chosen for the fluid collection system 10. While the strips 40 may be attached to the fluid collection system in any number of ways and positions, in the preferred embodiment, the strips 40 in the troughs 30 and 32 are folded into a "V" shape and attached to the interior surfaces of the troughs 30 and 32 by adhesives or other means. Once the pouch is in place on the patient or on the drape, the open ends of the "V's" of the malleable strips 40 can be spread apart to keep the troughs open. The malleable strip 40 located parallel to the open top end 20 of pouch 28 is initially a flat strip. Once the pouch is in place, the strip 40 may be bent or formed into a convex or semi-circular shape to keep the from panel 12 of the open top end 20 of the pouch 28 spaced apart from the rear panel 14. Thus, these malleable strips 40 permit the troughs 30 and 32 and/or the opening 20 in the pouch 28 to remain open, thereby reducing the chance of fluid spilling and splash-over onto unintended areas of the drape 50 and the general operating area.

Figure 7:
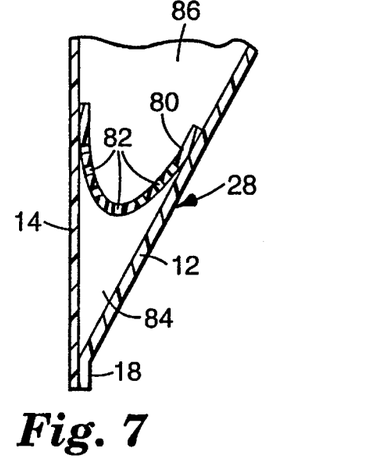

During an operation, many instruments, sponges, etc., are used. At the end of the operation, all such items must be collected and counted as a precautionary measure to ensure that none of them are left within the body cavity. Should any of these items fall into the fluid collection pouch 28, they could block the drain opening 26 and their removal from the fluid collection pouch 28 might prove difficult and/or dangerous. As a result, the fluid collection pouch 28 may be provided with a sieve 80 to trap objects which might find their way into the pouch. This sieve 80 is shown in phantom in FIGS. 1a, 1b, 3a and 3b and in cross-section in FIG. 7. Turning to FIG. 1b, the sieve 80 is positioned inside the fluid collection pouch 28 adjacent the opening 20. The sieve 80 has a plurality of perforations, slits or small holes 82 to allow the passage of fluids into the lower portion 84 of the pouch 28 while retaining solid objects such as instruments and sponges within the upper portion 86. The sieve 80 is connected to the front panel 12, rear panel 14 and edges 16 and 18 of fluid collection pouch 28, preferably by heat sealing or other suitable means which will permit the sieve 80 and pouch 28 to expand and remain open during use.

Figure 3A:
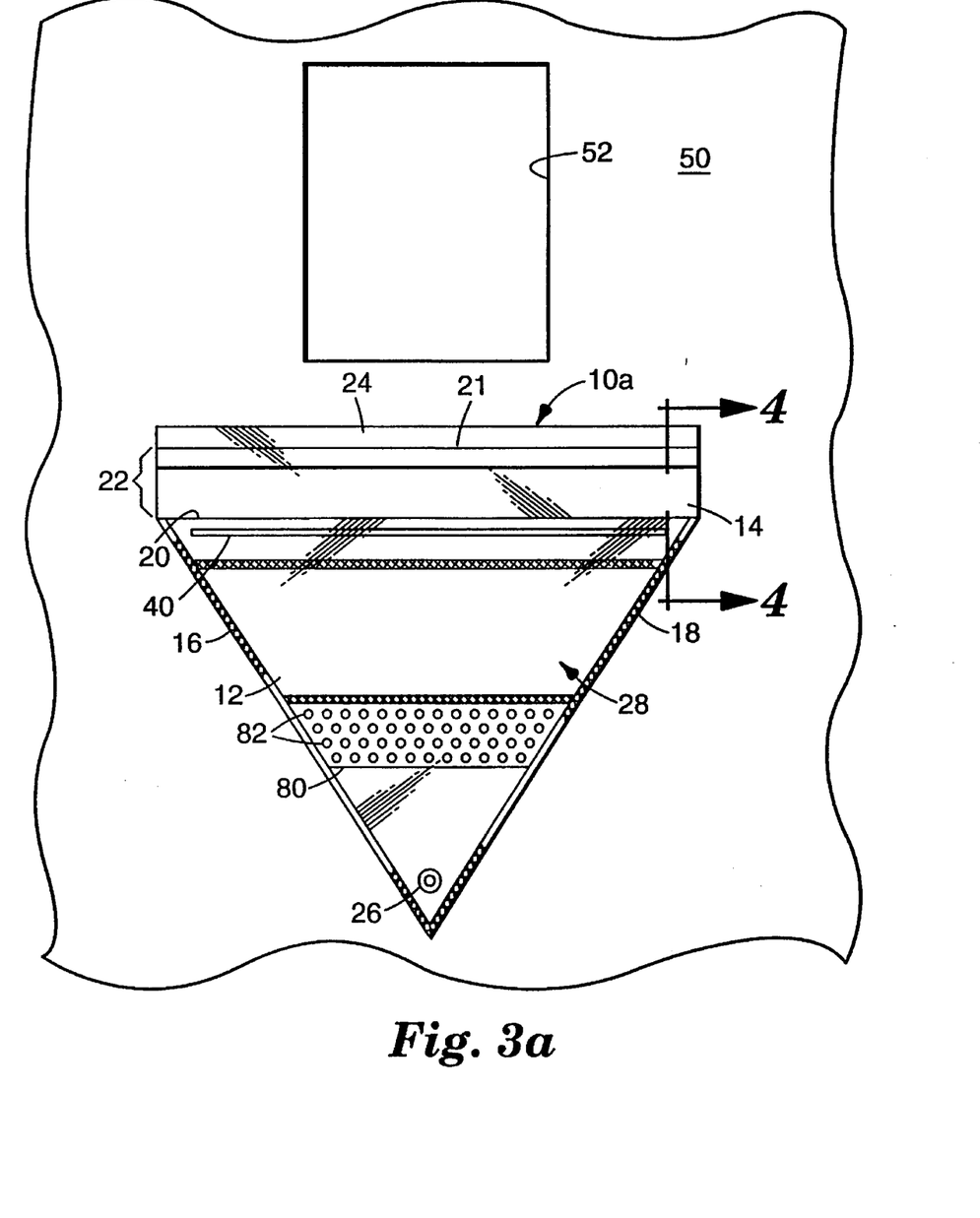
FIGS. 3a is a top plan view of a surgical drape and fluid collection system according to the present invention.
Figure 3B:
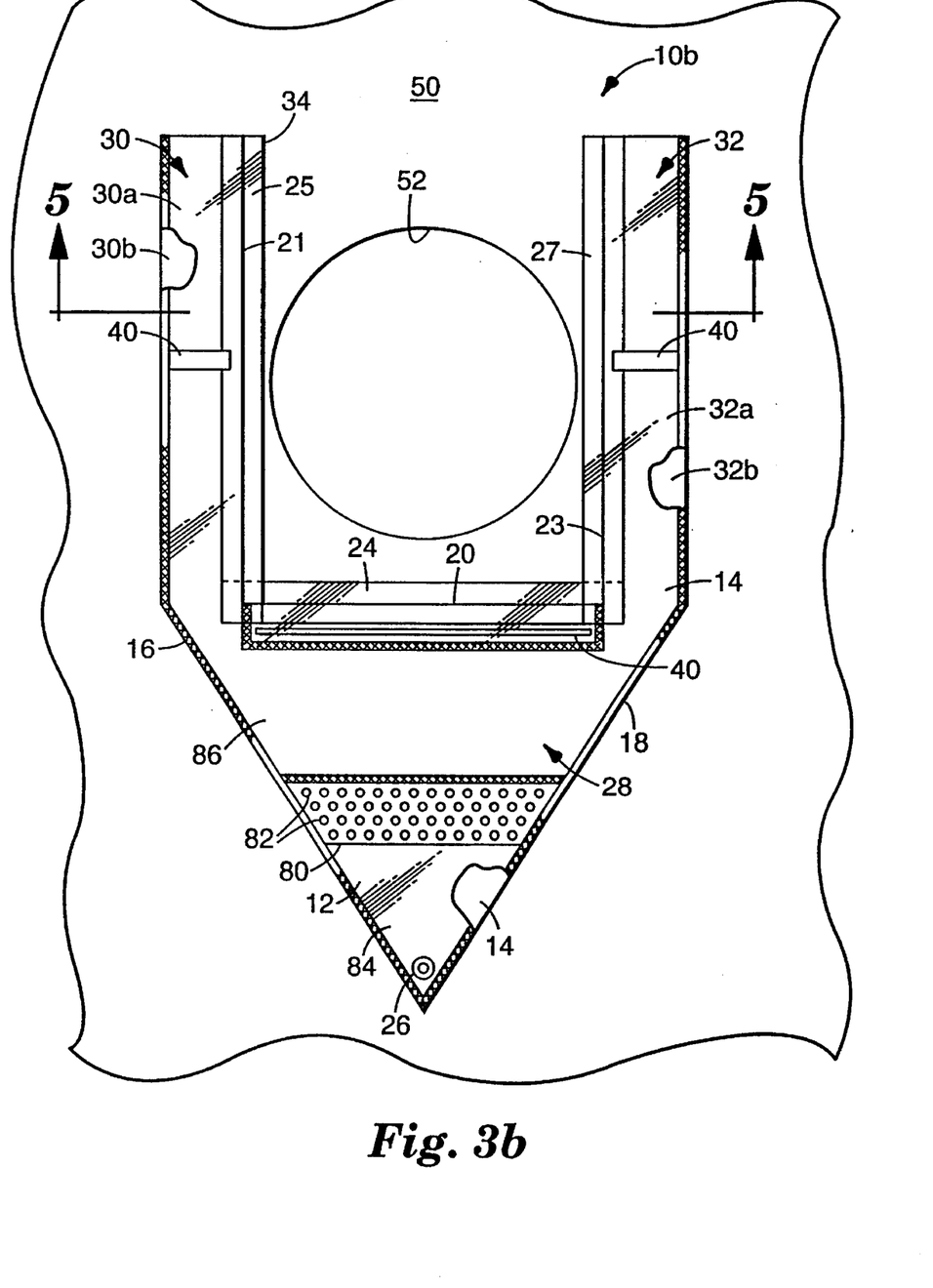
FIG. 3b is a top plan view of a surgical drape and fluid collection system according to the present invention.
Figure 4:
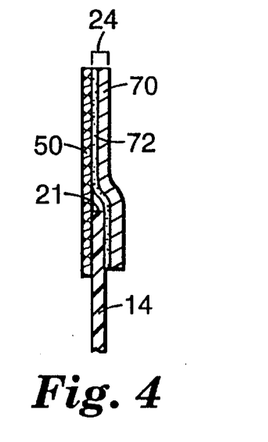
Figure 5:
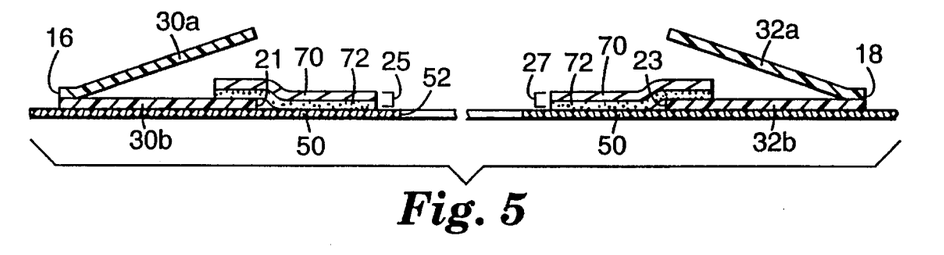
FIG. 5 is a cross-sectional view of the surgical drape and fluid collection system of FIG. 3b taken along line 5—5 of FIG. 3b.

Referring to FIGS. 3a and 3b, in use the sterilized drape 50 is placed over the patient such that the fenestration 52 is centered over the incision area and such that the fluid collection pouch is positioned in the expected path of fluid run-off. Once the drape is in place, the front panels 30a and 32a and the open top end 20 of fluid collection pouch 28 may be opened and maintained in the open position with the aid of the malleable strips 40. In so doing, fluids from the operation will be channeled into the fluid collection pouch 28 where they may be stored or removed via drain opening 26. FIG. 4 illustrates a cross-section of the drape system of the present invention along line 4—4 of FIG. 3a. As can be seen from this cross-section, the tape attachment strip provides a ramp over which fluid may easily flow. Notably, this cross-section is very much exaggerated in thickness. The actual tapes used in this invention are much thinner in cross-section.

As shown in FIG. 1a, the fluid collection pouch comprises a tape attachment strip 24 along and covering the leading edge 21 of the rear panel of the pouch 28. For ease of assembly, the rear panel of the pouch preferably has a rectangular flap 22 to which is attached a portion of the tape attachment strip 24. Alternatively, (not shown) for pouches without this tab the tape attachment strip may be attached directly to the rear panel of the pouch (i.e., along the open top end 20). Suitable tape attachment strips include the pressure sensitive adhesive tapes discussed herein. The tape attachment strips comprises an adhesive layer and a backing layer. To protect the adhesive surface from contamination, the adhesive surface is preferably covered with a liner prior to use. As shown in FIG. 1b, pouches comprising troughs 30 and 32 further comprise tape attachment strips (25 and 27) along the edge of lower flaps 30b and 32b of the troughs. Tape attachment strips 25 and 27 preferably overlap or underlap tape attachment strip 24 at each corner.

Figure 2A:
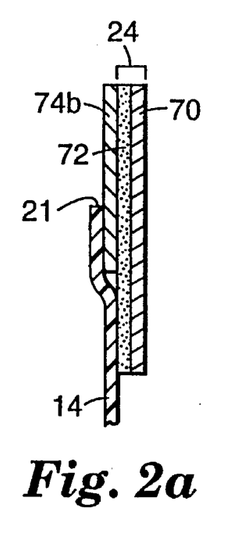
Figure 2B:
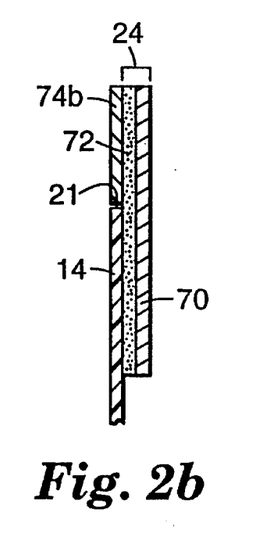
Figure 2C:
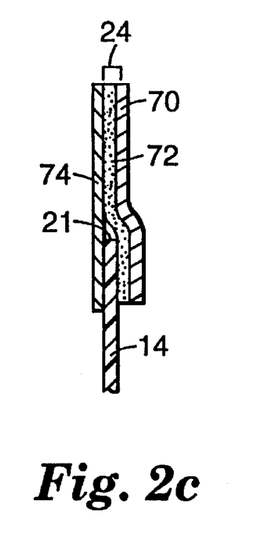

Referring to FIGS. 2a, 2b, and 2c, various alternative embodiments of the present invention are illustrated. In particular, three alternative methods of attaching the tape attachment strip to the rear panel of the pouch are shown. In FIG. 2a, a particularly preferred embodiment is shown. Tape 24 comprises backing 70 and adhesive layer 72. Prior to attachment to the pouch, the entire surface of adhesive layer 72 was preferably covered with a liner 74. A first portion 74a of the liner (not shown) is removed to expose a portion of adhesive layer 72. The exposed portion of adhesive layer is then contacted against the rear panel of the pouch. In FIG. 2a, a portion of the rear panel of the pouch overlaps the remaining portion 74b of the liner. This ensures that no portion of exposed adhesive is uncovered. Alternatively, as shown in FIG. 2b the remaining portion 74b of liner may butt up to the edge of the rear panel of the pouch. Preferably, no gap or only a minimal gap between the edges of the pouch and liner would exist. Also alternatively, and as shown in FIG. 2c, the tape attachment strip (comprising backing 70 and adhesive layer 72) is initially covered with a liner 74. Between a portion of the liner and the adhesive tape is placed the edge of the rear panel of the pouch. This may be accomplished, for example, by peeling the tape from the liner, attaching the pouch to a portion of the tape, and then re-attaching the liner to the tape. In all of the above embodiments, that portion of the liner which covers the adhesive layer of the tape is removed to expose the adhesive. The tape may then be placed against the drape to secure the pouch to the drape. FIG. 6 illustrates one method of attaching the tape attachment strip to the lower flap of troughs 30 and 32 (similar to the attachment method shown in FIG. 2a) along the line 6—6 of FIG. 1b.

Figure 8:
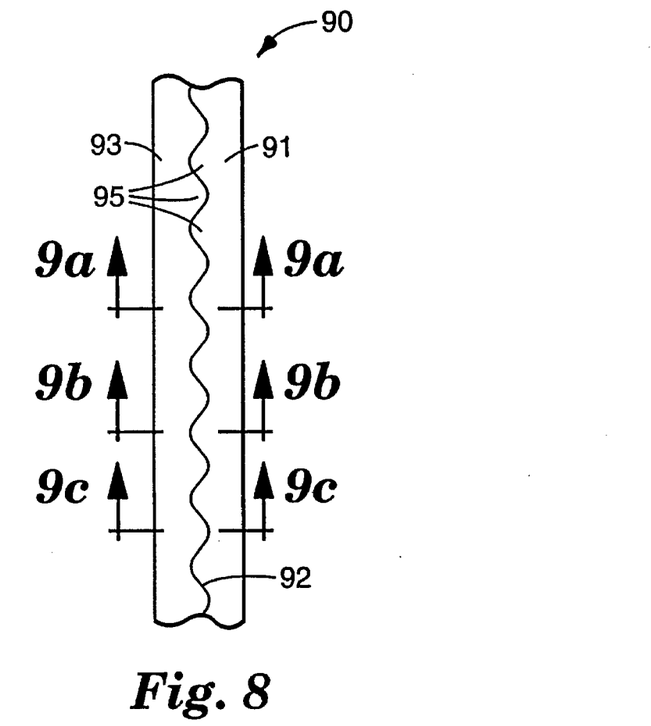
FIG. 8 is a plan view of the liner side of an alternative tape attachment strip of the present invention, wherein the liner has been slit lengthwise using a sinusoidal pattern.

FIG. 8 depicts the liner side an alternative tape attachment strip of the present invention. The tape attachment strip 90 has a two-piece liner attached to the adhesive side of the tape. The liner pieces 91 and 93 are separated along a sinusoidal line 92. When the tape is flexed in the manner depicted in FIGS. 9b and 9c, a portion 95 of the preferably somewhat stiffer liner separates from the adhesive tape and provides tabs which may be grasped by a user, thus facilitating the peeling of the liner from the tape. FIG. 9a illustrates a cross-section of the tape attachment strip of FIG. 8 prior to the tape being flexed. FIGS. 9b and 9c illustrate the cross-sections of the tape attachment strip along line B—B and C—C of FIG. 8 when the tape is being flexed. Notably, that portion of the liner 95 which crosses the midline of the tape separates from the tape when the tape is flexed.

FIGS. 10a and 10b depicts the liner side of a presently preferred tape attachment strip of the present invention. The tape attachment strip 100 has a two-piece liner attached to the adhesive side of the tape (shown in cutaway as backing 102 and adhesive layer 104). The liner pieces 106 and 108 are separated along slit 107. Liner piece 106 is generally removed by the manufacturer when the tape attachment strip is attached to a fluid collection pouch. Liner piece 108 is then removed thereby exposing an additional surface of adhesive which is used to attach the pouch to a surface. To facilitate removal of liner piece 108 by the health care provider, the manufacturer may create a "tab" of liner 114 by separating the liner from the tape at the end of the tape and folding the adhesive tape as depicted in FIG. 10b. Preferably, a corner of the adhesive tape is folded onto itself (e.g., positioning edge 110 parallel to slit 107), thereby covering a portion of the exposed adhesive. Liner 108 is preferably folded back on itself thereby creating crease line 113, wherein one end 112 of crease line 113 is positioned, preferably, to just overlap edge 111 of the folded tape corner. Preferably, liner 108 is folded in a manner such that crease line 113 and slit 107 form an angle between 45 and 80 degrees. This angled fold facilitates the peeling of liner 108 without tearing the liner. More preferably, crease line 113 and slit 107 form an angle between 60 and 75 degrees.

The following examples are offered to aid in the understanding of the present invention and are not to be construed as limiting the scope thereof. Unless otherwise indicated, all parts and percentages are by weight.

EXAMPLES

Example 1

Fluid Collection Pouch with Tape Attachment Strip

A fluid collection pouch suitable for attachment to a surgical drape or a patient's skin was produced in the following manner. The open top end of a commercially available irrigation pouch (available from 3M Co., St. Paul, Minn. as "STERI-DRAPE, Irrigation Pouch" Part No. 1016) was modified as follows. First, the double-sided adhesive tape which is provided with this pouch on the backside of the rear panel was removed by severing that portion of the flap which was covered with the double-sided tape. This left a rectangular flap portion which measured approximately 120 mm long by 500 mm wide. Along the edge of the flap was applied, as herein described, a 470 mm long piece of a commercially available single-sided adhesive tape (available from 3M Co., St. Paul, Minn. as No. 1526SL transparent 0.13 mm polyethylene medical tape). This adhesive tape measures 50.8 mm in width and has a liner covering the adhesive side of the tape. The liner has been slit into two narrower strips of material (measuring approximately 12 and 47.8 mm, respectively). The narrower strip of liner was removed by peeling the liner from the adhesive and the exposed adhesive was placed against the frontside of the flap along the edge of the flap. A portion of the wide strip of liner overlapped the edge of the flap by up to about 3 mm.

In use, the wide strip of liner is removed thus exposing the rest of the adhesive. The exposed adhesive may then be placed against the surface to which the pouch is being attached (such as a patient's skin or a surgical drape). Fluid is able to easily flow across the tape and into the pouch.

Various modifications and alterations of this invention will be apparent to those skilled in the art without departing from the scope and spirit of this invention, and it should be understood that this invention is not limited to the illustrative embodiments set forth herein.

What is claimed is:

1. A fluid collection pouch, comprising:
   a front panel and a rear panel joined along common side edges to form a fluid receiving chamber with a normally open top end, the front and rear panels having inside surfaces forming walls of the chamber;
   a rigid opening member attached to the pouch that maintains the front panel and the rear panel in a separated state thereby defining the open top end;
   a tape attachment strip having a backing and an adhesive layer covering one side of said backing, wherein a first portion of said tape attachment strip is adhesively attached to the inside surface of said rear panel along said open top end and wherein a second portion of the tape attachment strip overhangs the rear panel and is not adhesively attached to the rear panel; and
   a liner covering the adhesive layer of the second portion of said tape attachment strip,
   wherein the tape attachment strip provides a ramp over which fluids may easily flow into the pouch.

2. The fluid collection pouch of claim 1, wherein said front panel and said rear panel are generally triangular shaped and wherein two sides of said panels are joined, thereby defining said fluid receiving chamber.

3. The fluid collection pouch of claim 1, wherein said front panel and said rear panel each comprise:
   a generally triangular shaped portion having a first top edge with opposite ends, a second side edge, and a third side edge; and a pair of generally rectangular portions positioned parallel to each other and extending outwardly from the opposite ends of the first top edge of said triangular portion, each rectangular portion having an outer edge and an inner edge, wherein said panels are joined along the second and third side edges of said triangular portions of said panels and along the outer edges of said rectangular portions of said panels, thereby defining said fluid receiving chamber and a pair of troughs, the pouch further comprising:

a pair of additional tape attachment strips; and a pair of additional liners, wherein a first portion of the additional tape attachment strips are adhesively attached to the inside surface of said rear panel along the inner edges of said rectangular portions of said rear panel and wherein said additional liners cover second portions of said tape attachment strips which are not attached to said rear panel.

4. The fluid collection pouch of claim 1, wherein said fluid receiving chamber further comprises a sieve adjacent the open top end.

5. The fluid collection pouch of claim 4, wherein said fluid receiving chamber further comprises a drainage opening.

6. The fluid collection pouch of claim 1, wherein said pouch further comprises at least one malleable opening strip adapted to separate said front panel and said rear panel.

7. The fluid collection pouch of claim 1, wherein said fluid collection pouch comprises a material selected from the group consisting of acetate, ethylene vinyl acetate, acrylic, nylon, polypropylene, polyethylene, and polyester.

8. The fluid collection pouch of claim 1, wherein said front panel and said rear panel comprise a heat-bondable, fluid impervious material.

9. The fluid collection pouch of claim 1, wherein said tape attachment strip comprises a single-sided pressure sensitive adhesive tape.

10. The fluid collection pouch of claim 9, wherein said tape attachment strip further comprises a liner which has been slit lengthwise and which covers only a portion of said adhesive layer.

11. The fluid collection pouch of claim 10, wherein said slit defines a straight line.

12. The fluid collection pouch of claim 10, wherein said slit defines a curved line.

13. The fluid collection pouch of claim 1, wherein said adhesive layer comprises a pressure sensitive adhesive selected from the group consisting of copolymers of acrylate or methacrylate esters and an ethylenically unsaturated compound, copolymers of styrene and butadiene, and copolymers of styrene and isoprene.

14. The fluid collection pouch of claim 1, wherein said adhesive layer comprises a water-dispersible pressure sensitive adhesive.

15. An article, comprising: the fluid collection pouch of claim 1 and a surgical drape, wherein said pouch is attached to said surgical drape.

16. A surgical drape, comprising:

a sheet of drape material having a fenestration therein and a top surface;

a fluid collection pouch comprising a front panel and a rear panel joined along common side edges to form a fluid receiving chamber with a normally open top end, the front and rear panels having inside surfaces forming walls of the chamber;

a rigid opening member attached to the pouch that maintains the front panel and the rear panel in a separated state thereby defining the open top end;

a tape attachment strip having a backing and an adhesive layer covering one side of said backing, wherein a first portion of said tape attachment strip is adhesively attached to the inside surface of said rear panel of said pouch along said open top end and a second portion of said tape attachment strip is adhesively attached to the top surface of said sheet of drape material near said fenestration, thereby providing a ramp over which fluids easily may flow.

17. The surgical drape of claim 16, wherein said sheet of drape material comprises a reusable material.

18. The surgical drape of claim 16, wherein said sheet of drape material comprises a disposable material.

19. A method of attaching a fluid collection pouch to a surface, comprising the steps of:

providing a fluid collection pouch comprising a front panel and a rear panel joined along common side edges and defining a fluid receiving chamber therein and having a normally open top end, a rigid opening member attached to the pouch that maintain the front panel and the rear panel in a separated state thereby defining the open top end, and a tape attachment strip having a backing, an adhesive layer covering one side of said backing, and a liner, wherein a first portion of said tape attachment strip is adhesively attached to said rear panel along said open top end, a second portion of the tape attachment strip overhangs the rear panel and is not adhesively attached to the rear panel, and wherein said liner covers the adhesive layer of the second portion of said tape attachment strip;

removing said liner thereby exposing said adhesive layer; and contacting said exposed adhesive against said surface, wherein the tape attachment strip provides a ramp over which fluids may easily flow into the pouch.

20. A method of making a fluid collection pouch, comprising the steps of:

joining a front panel having an inside surface and outside surface and a rear panel having an inside surface and outside surface along common side edges, thereby defining a fluid receiving chamber therein and an open top end;

providing a tape attachment strip having a backing, an adhesive layer covering one side of said backing, and a liner, wherein said liner is slit lengthwise into at least two narrower strips;

removing one of said liner strips, thereby exposing a first portion of said adhesive layer; and contacting said exposed first portion of adhesive against the inside surface of said rear panel along said open top end.

* * * * *